United States Patent [19]

Lin

[11] Patent Number: 4,892,687

[45] Date of Patent: Jan. 9, 1990

[54] PROCESS FOR SYNTHESIS OF AMIDOACIDS USING A COBALT CATALYST AND A BIDENTAL PHOSPHINE LIGAND

[75] Inventor: Jiang-Jen Lin, Round Rock, Tex.

[73] Assignee: Texaco Inc., White Plains, N.Y.

[21] Appl. No.: 916,770

[22] Filed: Oct. 8, 1986

[51] Int. Cl.$^4$ ............... C07C 102/00; C07C 102/06; C07C 103/44; C07C 103/48; C07C 103/50
[52] U.S. Cl. .................................. 260/404; 560/253; 562/406; 562/518; 562/522; 564/132; 564/155; 564/157; 564/159
[58] Field of Search ............... 562/406, 522, 518; 564/159, 155, 132, 157; 560/233, 253; 260/404

[56] References Cited

U.S. PATENT DOCUMENTS

| | | | |
|---|---|---|---|
| 3,448,157 | 6/1969 | Slaugh et al. | 568/454 |
| 3,766,266 | 10/1973 | Wakamatsu et al. | 562/518 |
| 4,264,515 | 4/1981 | Stern et al. | 562/522 |
| 4,374,752 | 2/1983 | Argento et al. | 560/232 |

*Primary Examiner*—Vivian Garner
*Attorney, Agent, or Firm*—Jack H. Park; Kenneth R. Priem; Cynthia L. Kendrick

[57] ABSTRACT

A process is disclosed for producing N-acetyl-aminoacid which comprises reacting a feedstock from the group consisting of simple olefins, acetamide and synthesis gas with a catalyst comprising a cobalt-containing compound promoted by a bidental-phosphine ligand in a solvent at a pressure of 500 psi or greater and a temperature of 50° C. or greater. The presence of the ligand increases both reaction rate and cobalt catalyst stability.

12 Claims, No Drawings

PROCESS FOR SYNTHESIS OF AMIDOACIDS USING A COBALT CATALYST AND A BIDENTAL PHOSPHINE LIGAND

FIELD OF THE INVENTION

This invention relates to the synthesis of amido acids from olefins, acetamide and syngas.

More particularly this invention uses a cobalt catalyst promoted by a bidental-phosphine ligand to synthesize amido acids from olefins with 2 to 18 carbon atoms, internal olefins or allyl acetate, along with acetamide and synthesis gas in high yield with greater stability of the cobalt catalyst using low pressures and temperatures.

BACKGROUND OF THE INVENTION

Early attempts were unsuccessfully made to synthesize-α-amino acids or derivatives thereof by reacting a Schiff base or a nitrile with carbon monoxide and hydrogen. [Bull. Chem. Soc. Japan 33 (160) 78]

U.S. Pat. No. 3,766,266 to Wakamatsu discloses a method of producing an N-acyl-α-amino acid which comprises holding an aldehyde, an amide of a carboxylic acid and carbon monoxide at a temperature of 10° C. to 300° C. and a pressure of at least 500 atm. in the presence of a carbonylation catalyst until said N-acyl-α-amino acid is formed.

In *Chem. Comm.* 1540 (1971), Wakamatsu, et al. disclose a cobalt-catalyzed reaction which gives various N-acyl amino-acids from an aldehyde, an amide and carbon monoxide. In this disclosure, while benzaldehyde was used as the starting aldehyde, there was no corresponding α-phenyl-substituted amino acid obtained. Instead of the expected amino acid product, an imine was obtained by a simple "amination" reaction.

An article by Parnaud, et al., in *Journal of Molecular Catalysis*, 6 (1979) 341–350, discusses the synthesis potential and the catalytic mechanism for the reaction wherein N-acyl-α-amino acids are produced by reacting an aldehyde, CO and an amide in the presence of dicobalt octacarbonyl.

In amidocarbonylation, the aldehyde can be generated in situ from allyl alcohol, alkyl halides, oxiranes, alcohols and olefins followed by the reaction with an amide and carbon monoxide to produce an N-acyl-α-amino acid.

A related Patent, U.S. Pat. No. 3,996,288 discloses that when an alcohol or certain of its ester derivatives is held at 50° C. to 200° C. and 10 to 500 atm. in the presence of hydrogen, carbon monoxide, the amide of a carboxylic acid and a carbonylation catalyst, an aldehyde having one more carbon atom than the alcohol or ester is formed in good yield. If the amide has at least one active hydrogen atom on its amide nitrogen, it further reacts with the aldehyde and carbon monoxide to form an N-acylamino acid.

Hirai, et al. discuss a process for combining the transition metal catalyzed isomerization of allyl alcohol to aldehyde and cobalt catalyzed amidocarbonylation to provide a route from allylic alcohols to N-acyl-α-amino acids. See *Tetrahedron Letters*, Vol. 23, No. 24, pp. 2491–2494, 1982.

U.S. Pat. No. 4,264,515 by R. Stern et al. discloses a process for obtaining terminal N-acyl-α-amino acids by a reaction catalyzed by a cobalt carbonylation catalyst wherein the aldehyde is produced in situ from olefins and $CO/H_2$ mixtures. An unsaturated vegetable oil or $C_8$–$C_{30}$ monoolefinic compound is reacted with an amide, carbon monoxide and hydrogen in the presence of a cobalt catalyst. The process is operated in one step and provides for increased selectivity.

Cobalt and rhodium catalysts have been used in the past for synthesis of amido acids.

In Applicant's copending application, Ser. No. 06/720,248, now abandoned, it was found that the use of a combined $HRh(CO)PPh_3)$-$Co_2(CO)_8$ catalyst afforded more stability to the dicobalt octacarbonyl catalyst and allowed the reaction to proceed at a lower temperature and pressure than with dicobalt octacarbonyl alone.

Murata, et al. disclose the results of research wherein methylacrylate was hydroformylated in the presence of a $Co_2(CO)_8$ catalyst and a phosphine ligand. It was found that the various di(tertiary phosphine) ligands had distinct effects on activity. It is disclosed that previously the general conclusion in the art was that the addition of a phosphorous ligand to the hydroformylation catalyst would decrease the rate.

In this study, it was found that $HCo(CO)_2(P-P)$ is responsible for an increase in activity and, although attempts to isolate it were unsuccessful it was found that:

(1) The treatment of $Co_2(CO)_8$ with trialkylphosphine ($PR_3$) under the hydroformylation reaction conditions leads to the formation of $HCo(CO)_3(PR_3)$ and (2) Apparently diphos acts as a bidentate ligand.

See Bull. Chem. Soc. Jpn. 53, 214–218 (1980) $Co_2(CO)_8$-di(tertiary phosphine) complex for methyl acrylate reaction.

In *New Synthesis With Carbon Monoxide*, 1980, p. 53, Falbe discusses the characteristic features of ligand-modified cobalt catalysts. Features listed include:

(1) Increased stability of oxo catalysts.

(2) Reduced activity necessitating greater reactor volumes.

(3) Marked hydrogenation activity resulting in only alcohols and no aldehydes with about 15% of the olefin feed hydrogenated to paraffins.

(4) High n:iso product ratio. There is a discussion of cobalt catalysts in hydroformylation in *JOMC 1985, 283* No. 1–3, p. 226. In this study it was found that the chelate complex $HCo(CO)_2$ $(Bu_2PCH_2CH_2PBu_2)$ was found to be inactive as a catalyst for the hydroformylation of propene at 180° C. It was slowly transformed, however, under the reaction conditions into an active form.

The instant invention relies on a cobalt catalyst promoted by a bidentate phosphine ligand for the synthesis of N-acetylamino acids or alkyl N-acetylamino acids from alpha olefins or internal olefins, acetamide and syngas wherein yields of N-acetylamino acids are as high as 80% and the recovery of cobalt catalyst is as high as 85–100%. The presence of the ligand increases both reaction rate and cobalt catalyst stability. The reaction requires higher reaction temperatures and regioselectivity levels are lower. The products of internal olefins can be used as surface active agents, specialty surfactants and oil additives. The N-acetylamino acid products of the alpha olefins can be used as surfactants. The amido acid products of allyl acetate are useful in polyamide-ester synthesis.

SUMMARY OF THE INVENTION

This invention concerns a method for synthesizing amido acid which comprises contacting a mixture of olefins, acetamide and syngas (carbon monoxide and hydrogen) with a catalyst comprising a cobalt catalyst promoted by a bidental-phosphine ligand in the presence of a solvent at a pressure of at least 500 psi and a temperature of at least 50° C.

Alpha olefins are used to produce solid N-acetylamino acids in yields as high as 80%.

DETAILED DESCRIPTION OF THE INVENTION

In the narrower and more preferred practice of this invention N-acetylamino acids are prepared from a mixture of olefins, acetamide, carbon monoxide and hydrogen by a process which comprises contacting said mixture with a catalyst system comprising a cobalt-containing compound promoted by a bidental-phosphine ligand catalyst in a substantially inert solvent at a temperature of at least 50° C. and a pressure of at least 50 psi until substantial formation of the desired amino acid has been achieved.

The novel amino acid derivatives are in liquid or solid form at room temperature. When alpha olefins are the feedstock the products are predominantly linear alkyl-N-acetylamino acids, useful for surfactants, enhanced oil recovery and lubricants.

The reaction for producing linear alkyl-N-acetylamino acids from alpha olefins can be represented by the following equation:

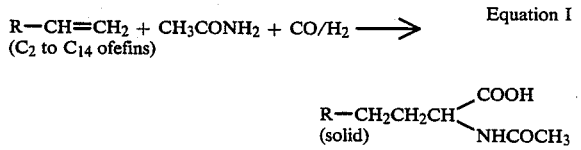

Equation I

The reaction for producing branched alkyl-N-acetylamino acids from internal olefins can be represented by the following equation:

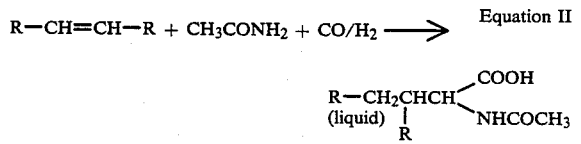

Equation II

The reaction for producing acetoxy-amidoacids from allyl acetate can be represented by the following equation:

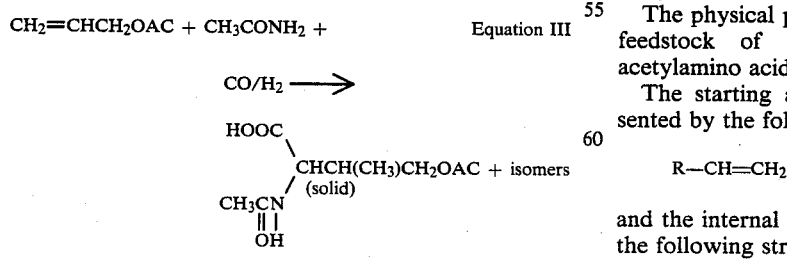

Equation III

Recovery of the amido acids from the reaction product can be carried out in any convenient or conventional manner such as by distillation, extraction, filtration, crystallization, etc. In the embodiment of this invention the product was recovered by a simple extraction procedure. The product was identified by H-nmr.

The catalyst system suitable for the practice of this invention comprises a cobalt catalyst and a bidental-phosphine ligand in a substantially inert solvent.

In the catalyst system of this invention the bidental-phosphine ligand and cobalt-containing compound are believed to be in complex equilibrium during amidocarbonylation. The controlled experiments represented by the Examples show the presence of both a bidental ligand and Co is essential to consistently produce the desired results. This catalyst system provides important advantages over the use of cobalt alone:

1. It affords an improved yield of amido acid from olefins.
2. It gives an increased reaction rate.
3. It allows for greater stability of the cobalt catalyst.

In the process of this invention it is preferable that the cobalt compound be used with a bidental-phosphine ligand. Compounds which work well in this respect include those where n=2, 3 or 6 for $Ph_2P(CH_2)_nPPh_2$. The preferred ligands for best recovery of the cobalt catalyst along with good selectivity for amido acids from alpha olefins are bis-1,2-(diphenylphosphino)ethane bis-1,3-(diphenylphosphino)propane and bis-1,6-(diphenylphosphino)hexane.

Bidental-phosphine ligands which work include those of the formula $-Ph_2P(CH_2)_nPPh_2$, especially where n=2 or 3. Among the bis(diphenylphosphino)alkane ligands studied, the effect of ligand on dicobalt octacarbonyl catalyst is dependent upon the species of $Ph_2P(CH_2)_n$ ligands. Where n=2 or 3, the bisphosphos ligands stabilize dicobalt octacarbonyl and enhance the catalyst activity, which is observed in the reaction of internal olefins (examples in the table). When n=1 or 4, the bisphosphos ligands deactivate the cobalt catalyst and show adverse effect on olefin conversion. When n=6, the ligand gave very high cobalt recovery after reaction.

The cobalt-containing compound may take many different forms. For instance, the cobalt may be added to the reaction mixture in the form of a variety of inorganic or organic cobalt salts, or cobalt carbonyls. The cobalt may, for example, be added as a cobalt halide such as cobalt bromide or cobalt chloride, or it may be added as the salt of an aliphatic or aromatic carboxylic acid such as, for example, cobalt formate, cobalt acetate, cobalt butyrate, cobalt naphthenate, and cobalt stearate. The cobalt carbonyl may be tetracobalt dodecacarbonyl or dicobalt octacarbonyl. The preferred cobalt-containing compound is dicobalt octacarbonyl.

The physical parameters which are desirable for the feedstock of this invention for producing N-acetylamino acid can be described as follows:

The starting alpha olefin substrates can be represented by the following structure $$R-CH=CH_2$$

and the internal olefin substrate can be represented by the following structure:

$$R-CH=CH-R$$

The R-group can be any alkyl, such as methyl, ethyl, hexyl or octyl and their combinations. The preferred alpha olefins include 1-octene and 1-tetradecene. Particularly good results are obtained using 1-tetradecene.

The olefin can also be an internal olefin such as an internal $C_{12}$ olefin. The feedstock can also be allyl acetate.

Suitable amide-containing coreactants that are useful in the amidocarbonylation reaction have the general structure:

where the $R_1$ and $R_2$ groups may be a combination of aryl, alkyl, arylalkyl and alkylaryl hydrocarbonyl radicals, or hydrogen, including the methyl, ethyl, butyl, n-octyl, phenyl, benzyl and chlorophenyl groupings. Examples of suitable amide coreactants include acetamide, benzamide, formamide, n-methylformamide, lauramide and n-methylbenzamide. The preferred coreactant is acetamide.

The carbon monoxide employed need not satisfy particular purity requirements although catalyst contaminants should be avoided if the reaction is intended to continue over an extended period. Particularly in continuous operations, but also in batch experiments, the carbon monoxide and hydrogen gas may also be used in conjunction with up to 10% by volume of one or more other gases. These other gases may include one or more inert gases such as argon, nitrogen and the like or they may include gases that may, or may not, undergo reaction under carbon monoxide hydrogenation conditions, such as carbon dioxide, hydrocarbons, such as methane, ethane, propane and the like, ethers, such as dimethyl ether, methyl ethyl ether and diethyl ether, alkanols, such as methanol, and the like.

As characterized above, this process is operated as a homogeneous liquid phase mixture. The reaction is preferably operated in an inert solvent. Preferred inert solvents are those which permit at least partial dissolution of the cobalt and rhodium catalyst precursors, the amide and the olefin. These are generally polar solvents, of the ester, ether, ketone, amide, sulfoxide or aromatic hydrocarbon type, for example.

Methyl and ethyl acetate are examples of suitable solvents. Other polar solvents are ethers, such as p-dioxane, methyl tertiary butyl ether, methyl tertiary amyl ether or tetrahydrofuran, tertiary amides, such as dimethyl formamide, dimethyl sulfoxide and ethylene carbonate.

The preferred solvents were p-dioxane and ethyl acetate.

The liquid or solid N-acetylamino acid products can be extracted by treating the product solution with base and acid aqueous methyl acetate, evaporating the solvent and drying the product to afford pure products.

In all these syntheses in order to achieve a high degree of selectivity the amount of carbon monoxide, olefin and amide present in the reaction mixture should be sufficient to at least satisfy the stoichiometry of the desired formation of N-acetylamino acid as shown in Equations I-III above. Excess carbon monoxide over the stoichiometric amount may be present and is desirable.

The quantity of bidental-phosphine ligand and cobalt-containing compound to be used in the catalyst system of the invention may vary. The process is conducted in the presence of a catalytically effective quantity of the active phosphine ligand and the active cobalt-containing compound which gives the desired product in reasonable yield. The reaction proceeds when employing as little as about 0.5 weight percent, and even lesser amounts of the bidental-phosphine ligand, along with as little as about 0.1 weight percent of the cobalt-containing compound based on the total weight of the reaction mixture. The upper concentration is dictated by a variety of factors including catalyst cost, partial pressures of carbon monoxide and hydrogen, operating temperature, etc. A bidental-phosphine concentration of from about 0.1 to about 10 weight percent in conjunction with a cobalt-containing compound concentration of from about 0.1 to about 10 percent, based on the total weight of the reaction mixture is generally desirable in the practice of this invention.

Particularly superior results are obtained when the above-noted components of the catalyst system are combined as follows on a molar basis: Bidental-phosphine ligand to cobalt-containing compound, 4:1 to 1:4.

The operating conditions may vary over a wide range. The reaction temperature may vary from 25° C. to 300° C. The preferred temperature is from 80° C. to 150° C. The pressure may range from 500 psi to 3000 psi or more. In the embodiment using internal olefins, it appears that higher selectivities are obtained when operating at more moderate pressures, in the range from 600 to 1000 psi. In the embodiment using alpha olefins, very good yields are observed using very mild pressures and temperatures, in the range of 600–1000 psi and 100°–140° C. respectively.

The amidocarbonylation reaction of this invention is best conducted in a carbon monoxide-rich atmosphere, although some hydrogen gas should also be present in order to achieve maximum cobalt catalyst activity. The hydrogen to carbon monoxide molar ratio in the reactor may be varied, for example, within the range from 20:1 to 1:20, but preferably it should be rich in carbon monoxide and the $H_2$:CO ratio should be in the range 5:1 to 1:5.

The desired products of the synthesis using alpha olefins are N-acetylamino acids, such as, $\alpha$-hexyl acetyl-$\alpha$-aminoacid, $\alpha$-octyl acetyl-$\alpha$-aminoacid, $\alpha$-tetradecyl acetyl-$\alpha$-aminoacid and $\alpha$-decyl acetyl-$\alpha$-aminoacid. Also formed are significant amounts of bis-acetamido products. Each of these products, including by-products can be recovered from the reaction mixture by conventional means, e.g. crystallization or filtration.

The desired products of the synthesis using internal olefins are, branched-alkyl and acetyl-$\alpha$-aminoacids.

The desired product of the synthesis using allyl acetate is $\alpha$-(3-acetoxy-propyl) or ($\alpha$4-acetoxy-butyl)acetyl-$\alpha$-aminoacids.

The novel process of the invention can be conducted in a batch, semi-continuous or continuous manner. The catalyst can be initially introduced into the reaction zone batchwise, or it may be continuously or intermittently introduced into such a zone during the course of the synthesis reaction. Operating conditions can be adjusted to optimize the formation of the desired amino acid product, and said material may be recovered by methods known to the art, such as filtration, recrystallization distillation, extraction and the like. A fraction rich in the catalyst components may then be recycled to the reaction zone, if desired, and additional products generated.

The products have been identified in this work by one or more of the following analytical procedures: viz, gas-liquid phase chromatography (glc), gas chromatography/infrared spectroscopy (GC/IR), nuclear magnetic resonance (nmr) and elemental analysis, or a combination of these techniques. Analysis have for the most part, been by molar weight; all temperatures are in degrees centigrade and all pressures in pounds per square inch (psi).

The yield (mole %) of N-acetylamino acid derivative in this synthesis using an olefin is estimated basis equation I using the formula:

$$\frac{\text{Moles of N—acetylamino acids obtained}}{\text{Moles of olefin charged}} \times 100\%$$

To illustrate the process of the invention, the following examples are given. Examples 1 to 15 demonstrate the method of using alpha olefins and internal olefins in the process of this invention. Examples 16 and 17 demonstrate the embodiment using allyl acetate. It is to be understood however, that the examples are given in the way of illustration and are not to be regarded as limiting the invention in any way.

EXAMPLE 1

A 300 ml stirred autoclave was charged with $Co_2(CO)_8$ (0.68g, 2 mmoles), bis-1,2(diphenylphosphino)ethane (0.21g, 0.50 mmoles), 1-tetradecene (9.8g, 0.05M), acetamide (2.9g, 0.05 M) and p-dioxane (20g). The system was purged with a mixture of $CO/H_2$ (1:1 molar ratio) and pressured to 100 psi. At 130° C., the pressure was raised to 800 psi and maintained at this pressure by incremental addition of the $CO/H_2$ mixture. After four hours, the reaction was terminated and the reaction mixture was analyzed by H-nmr and showed the presence of N-acetylamino acid (I) at ca. 85% selectivity,

(I)

based on converted 1-tetradecene. The cobalt analysis in product solution indicated ca. 95% cobalt recovery.

EXAMPLE 2 (Comparative)

The same experimental procedures of the previous example were repeated, except no ligand was added. The reaction mixture was analyzed by H-nmr indicating >80% of compound (I) was obtained. The cobalt analysis showed only 82% recovery.

EXAMPLE 3

The procedures of the previous example were repeated, except using bis-1,6-(diphenylphosphino)hexane (0.22g, 0.5 mmole) and 1-octene (6.7g, 0.05M). The results showed ca. 80% of alkyl-N-acetylamino acid product. The cobalt analysis indicated 92% in solution based on $Co_2(CO)_8$ charged.

EXAMPLE 4

A mixture of $Co_2(CO)_8$ (0.34g, 1 mm), bis(1,3-diphenylphosphino)propane (0.103g, 0.25 mmole), 1-tetradecene (9.8g, 0.05M), acetamide (3.0g, 0.05M) and ethyl acetate (20g) was used. The operating conditions were 800 psi ($CO/H_2=1:1$), 130° C. and 5 hours. The product distributions were 56% selectivity to alkyl-N-acetylamino acid and 11% selectivity to (II).

(II)

The cobalt analysis indicated 86% recovery.

The reactions of alpha-olefins indicated some advantages in using bidentate ligand in terms of cobalt recovery. A comparison of reaction rate was set forth in the reaction of internal olefin at 800 psi low pressure. This explanation follows Table I.

TABLE 1

LIGAND EFFECTS ON REACTION RATE - THE REACTION OF $C_{12}$ INTERNAL OLEFIN, ACETAMIDE AND COBALT CARBONYL CATALYST*

| Example | Ligand | Conditions** | CO—$H_2$ Consummed (psi) | Olefin conversion (%) | Cobalt Recovery (%) |
|---|---|---|---|---|---|
| 5 (Comparative) | None | 130° C. 4 hrs. | 90 | 68 | 81 |
| 6 | $Ph_2P(CH_2)PPh_2$ (0.38 g, 1 mm) | 130° C. 5 hrs. | 90 | 40 | 80 |
| 7 | $Ph_2P(CH_2)_2PPh_2$ (0.40 g, 1 mm) | 130° C. 4 hrs. | 390 | 80 | — |
| 8 | $Ph_2P(CH_2)_3PPh_2$ (0.412 g, 1 mm) | 130° C. 4 hrs. | 375 | 95 | 85 |
| 9 | $Ph_2P(CH_2)_4PPh_2$ (0.426 g, 1 mm) | 130° C. 4 hrs. | 200 | <60 | — |
| 10 | $Ph_2P(CH_2)_6PPh_2$ (0.45 g, 1 mm) | 130° C. 4 hrs. | 80 | 75 | 100 |
| 11 | $n\text{-}Bu_3P$ (0.202 g, 1 mm) | 130° C. 4 hrs. | 140 | 60 | — |
| 12 | $Ph_3P$ (0.52g, 2 mm) | 130° C. 4 hrs. | 390 | 90 | 68 |
| 13 | TMEDA (0.116 g, 1 mm) | 130° C. 4 hrs. | 15 | <20 | — |
| 14 | $Ph_2P(CH_2)_3PPh_2$ (0.412 g, 1 mm) | 150° C. 4 hrs. | 420 | 95 | 80 |
| 15 | None | 150° C. | — | ~0 | — |

TABLE 1-continued

LIGAND EFFECTS ON REACTION RATE - THE REACTION OF $C_{12}$ INTERNAL OLEFIN, ACETAMIDE AND COBALT CARBONYL CATALYST*

| Example | Ligand | Conditions** | CO—$H_2$ Consumed (psi) | Olefin conversion (%) | Cobalt Recovery (%) |
|---|---|---|---|---|---|
| (Comparative) | | 4 hrs. | | | |

*Materials used: $CO_2(CO)_8$ (0.58 g, 2 mm); i-$C_{12}$ olefin (17 g, 0.1M) acetamide (6 g, 0.1M); p-dioxane (30 g)
**Syngas Conditions: CO—$H_2$ (1:1), 800 psi
NOTES:
Exp. 5: Pink product solution
Exp. 6: Brown product solution
Exp. 7: Brown product solution
Exp. 8: Black product solution
Exp. 9: Brown product solution
Exp. 10: Brown product solution
Exp. 11: Brown product solution
Exp. 12: Brown solution with some solid precipitate
Exp. 13: Light color solution with precipitate
Exp. 14: Brown Product solution
Exp. 15: Brown solution The results in Table 1 were obtained in a 300 ml stirred autoclave with identical experimental procedures. The amount of gas consumption indicated the approximate, relative rate of olefin hydroformylation and amidocarbonylation to product alkyl-amido acids. It also represented the activity of the cobalt catalyst. The olefin conversion showed the initiated hydroformylation to form the aldehyde intermediate. The cobalt analysis in product solution, figured as a percentage based on dicobalt octacarbonyl charged should represent the stability of cobalt in solution under such reaction conditions. The total recovery of cobalt by no means represented the active species in the reaction. The active species might be lost as $HCo(CO)_4$ (gas) formed during the process. The significant features in these comparative examples are cited as follows:

(a) In comparison with $Co_2(CO)_8$ alone, the addition of some particular ligand increases the reaction rate of olefin conversion. The ligands $Ph_2P(CH_2)_3PPh_2$ and $Ph_2P(CH_2)_2PPh_2$ gave the best results (Exp. 7 and 8).

(b) Unsuitable ligands such as $Ph_2P(CH_2)PPh_2$, n-$Bu_3P$ and $Ph_2P(CH_2)_4PPh_2$ had adverse effects. This might be caused by geometric effect in cobalt-ligand complexes (Exp. 6, 9 and 11).

(c) TMEDA (tetramethylethylenediamine) hampered the cobalt activity (Exp. 13) and caused low olefin conversion.

(d) $Ph_3P$ was a good ligand in terms of the reactivity, but total cobalt recovery was low (Exp. 12).

(e) In general, the cobalt recovery in the solution was higher when a ligand was applied.

(f) It is important to note that at operating conditions of 150° C., 800 psi, dicobalt octacarbonyl decomposed (Exp. 15). The use of $Ph_2P(CH_2)_2PPh_2$, in contrast, offered a significantly improved result (Exp 14). It means the complex of $Co_2(CO)_8$-$Ph_2P(CH_2)_2PPh_2$ has better catalyst reactivity and stability.

EXAMPLE 16

A glass-lined reactor was charged with $Co_2(CO)_8$ (6.8g, 20 mmoles), acetamide (60g), allyl acetate (100g) and p-dioxane (100g). The reactor was flushed with CO/$H_2$=1:1 and pressured to 500 psi, then heated to 130° C. At this temperature, the pressure was raised slowly to 2000 psi, and maintained for two hours. The product mixture (310g, deep brown solution) was extracted with base and acid aqueous ethyl acetate solution, evaporated solvent and dried to afford ca. 87g pure products (III) (ca. 43%). H-nmr showed structures III and IV as follows:

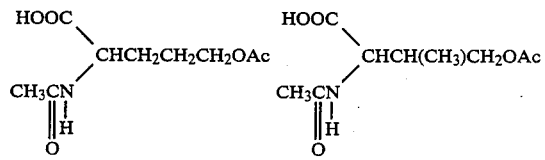

EXAMPLE 17

The same experiments were repeated, using $Co_2(CO)_8$ (0.68g, 2 mmole), acetamide (6g), allyl acetate (10g), p-dioxane (10g), and bis(1,4-diphenylphosphino)butane (1.70g, 4 mmoles). The mixture was subjected to conditions of 2000 psi CO/$H_2$=1:1, 130° C. and 2 hours. The recovery product mixture showed only allyl acetate recovery (>70%). The experiment showed the detrimental effect of using large amounts of bis(1,4-diphenylphosphino)butane ligand. In this case, once again, it demonstrated that a suitable bidental ligand is essential as indicated in Table 1.

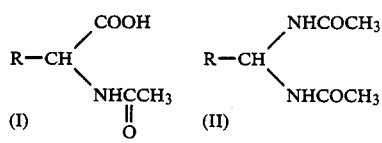

What is claimed is:

1. A process for producing novel N-acetyl-amino acid derivatives represented by the formula (I) and (II)

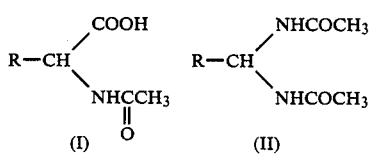

which comprises reacting a feedstock from the group consisting of alpha olefins with 2 to 20 carbons and internal olefins with 4 to 20 carbons, acetamide and synthesis gas with a catalyst comprising a cobalt-containing compound promoted by a bidental-phosphine ligand in a solvent at a pressure of at least 500 psi and a temperature of at least 50° C., wherein R can be any alkyl and wherein the bidental phosphine ligand is of the formula

wherein n=2, 3, or 6 and Ph represents phenyl.

2. The process of claim 1 wherein the alpha olefin is selected from the group consisting of 1-octene and 1-tetradecene.

3. The process of claim 1 wherein the internal olefin is an internal C$_{12}$ olefin.

4. The process of claim 1 wherein the bidentalphosphine ligand is selected from the group consisting of bis-1,2-(diphenylphosphino)ethane and bis-(1,3-diphenylphosphine)propane.

5. The process of claim 1 wherein the cobalt-containing compound is selected from the group consisting of cobalt carbonyls, cobalt halides and cobalt carboxylates.

6. The process of claim 1 wherein the cobalt-containing compound is selected from the group consisting of dicobalt octacarbonyl, cobalt(II) acetate, cobalt(II) chloride and cobalt(II) bromide.

7. The process of claim 1 wherein the cobalt-containing compound is dicobalt octacarbonyl.

8. The process of claim 1 wherein the synthesis gas pressure is a low pressure of about 500 psi to 1000 psi.

9. The process of claim 1 wherein the reaction temperature is in the range of 100° C. to 180° C.

10. The process of claim 1 wherein the solvent is selected from the group consisting of methyl acetate, ethyl acetate and p-dioxane.

11. A process for producing acetoxy-amidoacid derivatives, represented by the structural formulas (III) and (IV),

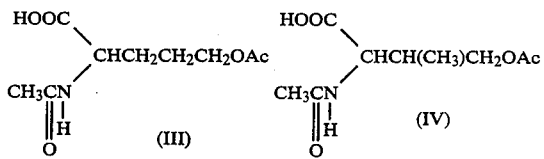

which comprises reacting allyl acetate, acetamide and synthesis gas with dicobalt octacarbonyl catalyst in a solvent at a pressure of 600 psi to 1000 psi and a temperature of 100°–150° C.

12. A process for producing novel N-acetyl-aminoacid derivatives which comprises reacting a starting material from the group consisting of 1-octene, 1-tetradecene, an internal C$_{12}$ olefin or allyl acetate and acetamide and synthesis gas with a catalyst comprising a cobaltcarbonyl compound promoted by a bidentalphosphine ligand of the formula

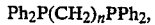

wherein n=2 or 3 and pH represents phenyl, in a solvent at a pressure of 600–1000 psi and a temperature of 100°–150°C.

* * * * *